US009086421B1

(12) United States Patent
Miller et al.

(10) Patent No.: US 9,086,421 B1
(45) Date of Patent: Jul. 21, 2015

(54) DEVICE AND METHOD FOR CAVITY DETECTED HIGH-SPEED DIFFUSION CHROMATOGRAPHY

(75) Inventors: Anthony Miller, San Francisco, CA (US); Jason McKeever, San Francisco, CA (US)

(73) Assignee: ENTANGLEMENT TECHNOLOGIES, INC., Burlingame, CA (US)

( * ) Notice: Subject to any disclaimer, the term of this patent is extended or adjusted under 35 U.S.C. 154(b) by 833 days.

(21) Appl. No.: 13/192,714

(22) Filed: Jul. 28, 2011

Related U.S. Application Data

(60) Provisional application No. 61/368,830, filed on Jul. 29, 2010.

(51) Int. Cl.
G01N 30/74 (2006.01)
G01N 30/20 (2006.01)
G01N 30/38 (2006.01)
G01N 30/46 (2006.01)
G01N 30/02 (2006.01)

(52) U.S. Cl.
CPC ............. *G01N 30/74* (2013.01); *G01N 30/02* (2013.01); *G01N 30/20* (2013.01); *G01N 30/466* (2013.01); G01N 2030/204 (2013.01); G01N 2030/385 (2013.01)

(58) Field of Classification Search
CPC ..... G01N 21/39; G01N 21/274; G01N 30/02; G01N 30/20; G01N 30/466; G01N 2030/204; G01N 2030/385
USPC .............. 73/23.39, 23.4, 23.41, 23.42, 61.53, 73/61.55, 61.56
See application file for complete search history.

(56) References Cited

U.S. PATENT DOCUMENTS 3,206,968 A 9/1965 Leggoe et al.
3,622,278 A * 11/1971 Elzinga et al. ................ 436/181
(Continued)

FOREIGN PATENT DOCUMENTS

WO 2010/042178 A2 4/2010

OTHER PUBLICATIONS

McHale, K. et al., "Bayesian Estimation for Species Identification in Single-Molecule Fluorescence Microscopy", Biophysical Journal, vol. 86, Jun. 2004, pp. 3409-3422.*
Ye et al., "Ultrasensitive detections in atomic and molecular physics: demonstration in molecular overtone spectroscopy," J. Opt. Soc. Am. B, vol. 15, No. 1, pp. 6-15, 1998.
Lehmann et al., "An Introduction to Cavity Ring-Down Spectroscopy—Cavity Ring-Down Spectroscopy: Techniques and Applications." Oxford: Blackwell, 2009.
(Continued)

*Primary Examiner* — Daniel S Larkin
(74) *Attorney, Agent, or Firm* — Rankin, Hill & Clark LLP

(57) ABSTRACT

A chromatography sensor device is provided that includes a first loading chamber into which a sample fluid can be inserted, a second loading chamber into which a buffer fluid can be inserted, a diffusion column adapted to communicate with the first loading chamber and the second loading chamber and having walls lined with a chromatography stationary phase, a first high finesse optical cavity communicating with the diffusion column at a first distance from the gate, a second high finesse optical cavity communicating with the diffusion column at a second distance from the gate; and one or more lasers for generating laser frequencies for exciting the first and second high finesse optical cavities, whereby the sample fluid may diffuse into the diffusion column containing the buffer fluid and the one or more lasers and associated detectors may be used to detect a molecule of interest in the sample fluid.

26 Claims, 9 Drawing Sheets

(56) References Cited

U.S. PATENT DOCUMENTS

| | | | |
|---|---|---|---|
| 4,375,163 A * | 3/1983 | Yang | 73/61.53 |
| 4,724,081 A * | 2/1988 | Kawahara et al. | 210/659 |
| 5,450,743 A * | 9/1995 | Buote | 73/61.56 |
| 5,528,040 A | 6/1996 | Lehmann | |
| 5,815,277 A | 9/1998 | Zare et al. | |
| 6,727,492 B1 | 4/2004 | Ye et al. | |
| 6,865,198 B2 | 3/2005 | Taubman | |
| 7,277,177 B2 | 10/2007 | Augustine et al. | |
| 7,538,881 B2 | 5/2009 | Ye et al. | |
| 7,916,395 B2 | 3/2011 | Cole | |
| 2010/0277737 A1 | 11/2010 | Tuchman et al. | |
| 2012/0090411 A1 * | 4/2012 | Perlinger et al. | 73/863.12 |

OTHER PUBLICATIONS

Stockton et al.; "Bayesian estimation for selective trace gas detection." Appl. Phys. B. 96 (2009): 567-570.

Mabuchi et al.; (1999). "Full observation of single-atom dynamics in cavity QED"; Applied Physics B Lasers and Optics, 1108, 1095-1108.

O'Keefe et al.; "cw Integrated cavity output spectroscopy," Chem. Phys. Lett., vol. 307, p. 343-349 (1999).

Thorpe et al; "Cavity enhanced optical frequency comb spectroscopy." Optics Express, vol. 16, No. 4, p. 2387 (2008).

* cited by examiner

DEVICE AND METHOD FOR CAVITY DETECTED HIGH-SPEED DIFFUSION CHROMATOGRAPHY

This application is a non-provisional application claiming priority to provisional application 61/368,830 filed on Jul. 29, 2010, the entirely of which is incorporated by reference.

STATEMENT REGARDING FEDERALLY SPONSORED RESEARCH

At least a portion of this invention was made under a contract with an Agency of the United States Government, namely: US Army Contracting Command (Night Vision and Electronic Sensor Directorate) Contract # W909MY-09-C-0077.

BACKGROUND OF THE INVENTION

1. Field of the Invention

This invention relates generally to the detection of trace gases.

2. Description of Related Art

Trace gas detection has applications ranging from explosive and chemical weapons detection to semiconductor manufacturing and medical diagnostics, which utilize a large range of platform technologies. Optical absorption spectroscopy is one technique to measure the presence and concentration of trace gases. For many applications extreme sensitivity is required due to the low concentrations and small optical interaction (optical cross sections) of common analytes.

Absorption measurements represent one leading technique for trace gas detection. Small changes in the transmitted intensity of a probe laser beam are used to determine the presence of absorbing species in a sample. Here, "laser" refers to any coherent source of electro-magnetic radiation, including but not limited to lasers, frequency-converted laser beams, harmonic generation from laser beams, optical parametric oscillators, and difference frequency generators. For 1 mW of incident laser radiation and 1 second measurement times, absorption sensitivities approaching $10^{-9}$/cm are in principle attainable. Precise stabilization of the laser intensity is generally seen as required for this technique. In practice, a much worse sensitivity is usually achieved. The sensitivity of absorption detection of trace gases can be enhanced by placing the absorbing sample in a high-finesse optical cavity which provides multi-pass interaction between the probe beam and the sample. The light can interact with a sample each time it reflects off the cavity mirrors, which can be greater than $10^5$ times (corresponding to cavity finesse, $F \sim 10^5$), as can be achieved with state of the art mirror technology in certain wavelength ranges.

A high finesse cavity is also a narrow frequency discriminator which only allows the transmission of a narrow range of frequencies. Therefore any frequency fluctuations in the probe laser are mapped onto amplitude fluctuations in the light transmitted through the cavity, which can further exacerbate the technical problem of intensity stabilization. One approach to circumventing this problem is cavity ring-down spectroscopy (CRDS), in which the time-decay curve of the intensity transmitted through the cavity is measured when the input light is terminated or the frequency of the input light is shifted away from the cavity resonance. The light intensity can be fit to a decay function, typically exponential, whose time constant (the cavity ring down time) is related to the cavity loss which includes absorption through the cavity.

One of the additional challenges in this arena is detecting target vapors that may be obscured by backgrounds with significantly stronger absorption at one or many optical wavelengths. A technique has been developed to use mass diffusion of molecules in the sample to detect weak absorbers in the presence of potentially far stronger backgrounds. This technique is however limited by the fact that diffusion coefficients of molecules vary only by the square root of the mass and the performance of the Bayesian Estimator (as described in Stockton, J. K., and A. K. Tuchman (2009)) is limited by differences in diffusion coefficients. An improved diffusion device and technique is desirable.

BRIEF SUMMARY OF THE INVENTION

Diffusion chromatography is a technique to detect multiple analyte species contained in a single sample by monitoring the spatial evolution of analyte concentrations over time. At the beginning of a measurement, a fluid sample containing analyte molecules is brought into contact with a diffusion column containing a buffer fluid. The analytes diffuse into the diffusion column. During the diffusion process, repeated measurements ("absorption measurements") are performed at one or more distances along the diffusion column. The measurements are generally sensitive to all analytes, so each measurement outcome will be a function of the concentrations of all analytes present and the time and location of the measurement. The concentrations of the various analytes are then estimated using a Bayesian Estimator or a similar statistical signal processing technique to use the full measured spatial and temporal profile to identify the concentrations of the analytes in the sample. The diffusion column has walls lined with a stationary phase. This stationary phase will modify the diffusion of the analytes by the retention coefficient of the stationary phase. This can be used to increase the dispersion of diffusion coefficients to improve detection sensitivity. In an alternative variation, the diffusion column instead has non-interacting walls in which case diffusion is set only by the free-diffusion of the analytes in the buffer.

Diffusion chromatography does not separate different analyte species so that they are independently resolved, and there the analyte molecules are not entrained in a "mobile phase". Instead, transport is entirely through diffusion within a stationary buffer. The diffusion chromatographer records a signal at one or many points in the diffusion column at one or many times during the diffusion process. Analyte species are distinguished because they will pass through the measurement locations with different temporal profiles depending on their diffusion coefficients.

This application includes by reference the entire disclosure of US Publication 20100277737 and WO 2010/042178. The teachings therein are extended here by using stationary phases from gas chromatography columns to modify the effective diffusion coefficients of molecules in a sample. The diffusion coefficient is modified by the partition of analyte molecules from the diffusion phase into the stationary phase where they remain effectively stationary. Consequently, the effective diffusion coefficient of an analyte will depend on the free diffusion coefficient and a partition coefficient of the analyte in the selected stationary phase. The sensitivity of the device to a specific analyte in the presence of other analytes depends on the relative difference in diffusion coefficients of the different analytes. A stationary phase is chosen to maximize the difference in diffusion coefficients between different analytes of interest.

Generally, gas chromatography takes many minutes to perform a separation. This is because long columns are required in order to separate different molecules. The method described herein has a detection performance that is independent of the length of the diffusion column over a wide range of diffusion column dimensions. The diffusion time is proportional to the square of the diffusion length, so by reducing the dimension of the device, measurements can be performed extremely quickly. Without a large column and thermally cycling oven, it is also possible to build a compact high-speed device taking advantage of many of the properties that make standard gas chromatography desirable.

In operation, at an initial time a gate is opened and the sample gas begins to diffuse down the length of the diffusion column. The rate of diffusion of any specific molecule will be determined by a combination of free diffusion rate of the molecule (in any fluid including gas or liquid) and the degree to which the molecule partitions into the stationary phase. Detection of analytes is performed at one or many locations within the diffusion column (one or many diffusion distances) and at one or many times after the gate is opened (one or many diffusion times). Optical absorption is one class of the many available detection techniques, and CRDS is one such optical absorption technique. Optical cavities in the diffusion column are used to measure the total absorption of the fluid mixtures present in the mode volume of each cavity at the exciting laser wavelengths. The cavities are arranged to measure the concentrations at a set of distances from the point where the gate is located. Different fluids will diffuse through the different cavities at different times. The optical detectors on the output of the cavities measure this absorption as a function of time since the gate was opened. These signal traces will then be fed into an estimator (for example, a Bayesian estimator) that is used to estimate the concentrations of different species present in the initial sample given their effective diffusion times and optical absorption cross sections at the laser wavelengths used. Although the invention applies to any fluid sample, for the remainder of this specification the fluid is assumed to be gas without loss of generality.

DETAILED DESCRIPTION OF THE INVENTION

A gas diffusion chromatography sensor device assembly and method for using the device to measure trace gases is described below. The device may be operated at a fixed or variable temperature set by the user.

Figure 1:
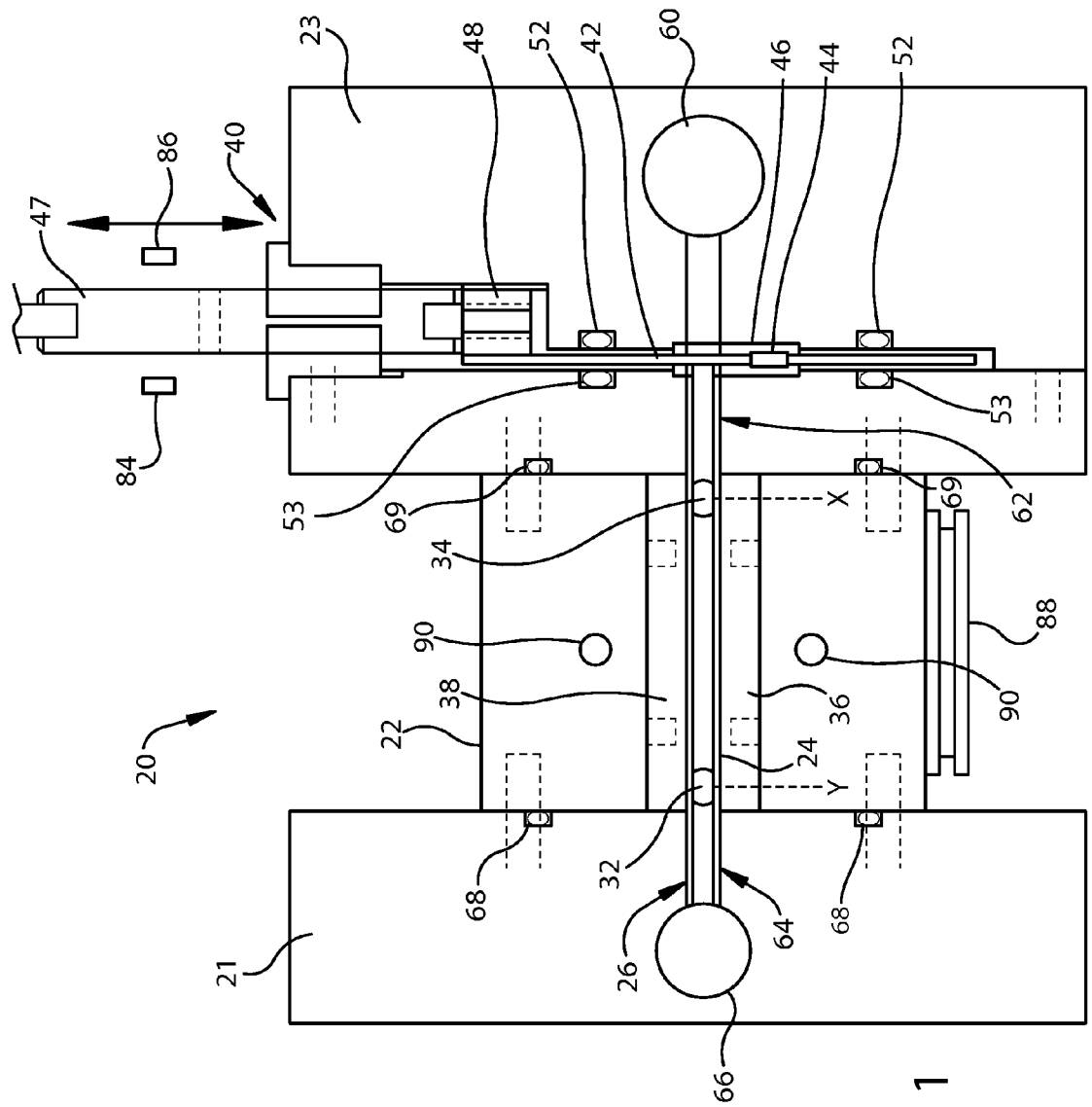
FIG. 1 is a cross sectional schematic side-view of a sensor assembly.
Figure 3:
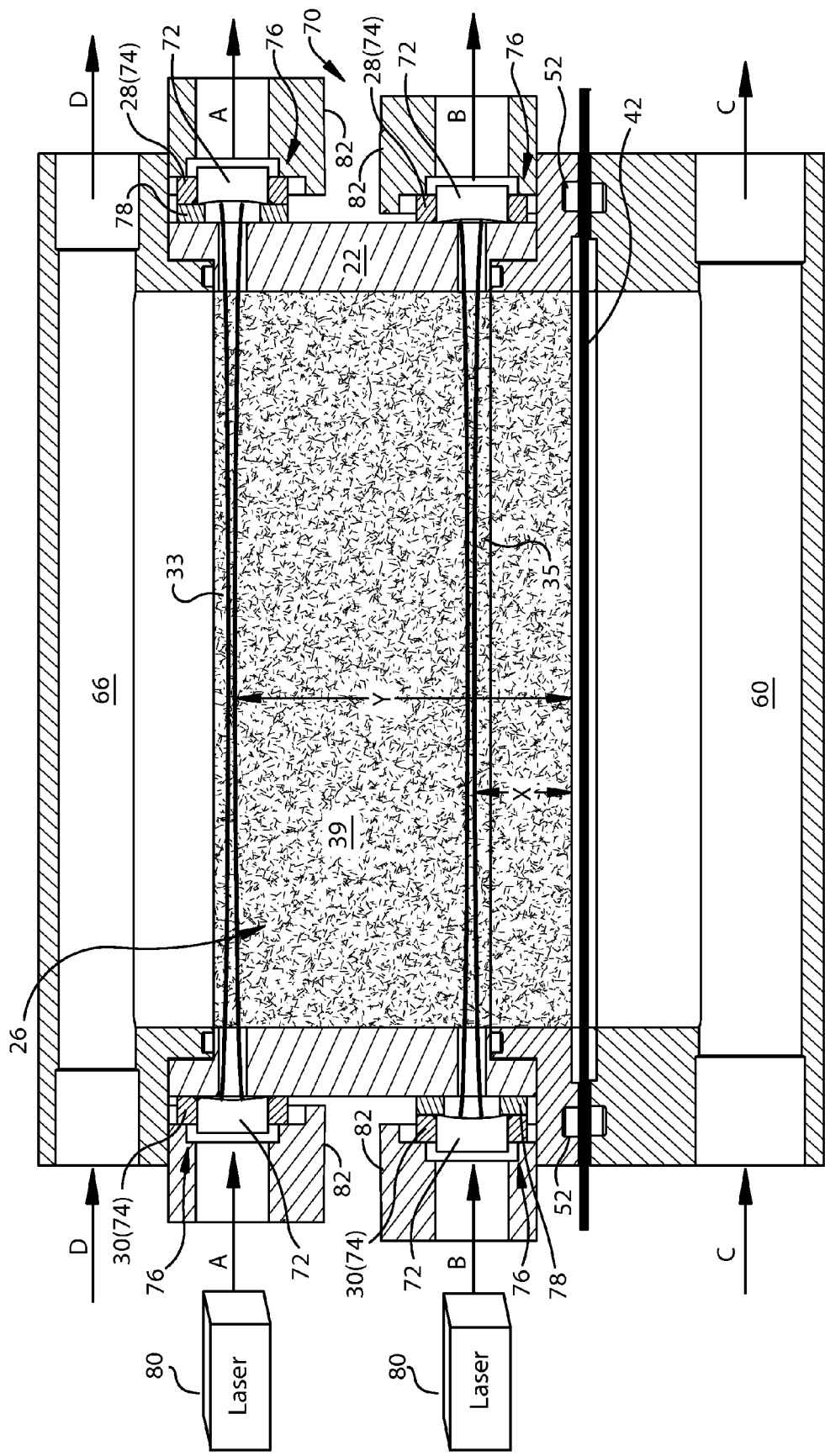
FIG. 3 is a cross sectional schematic top-view of the sensor assembly.
Figure 7:
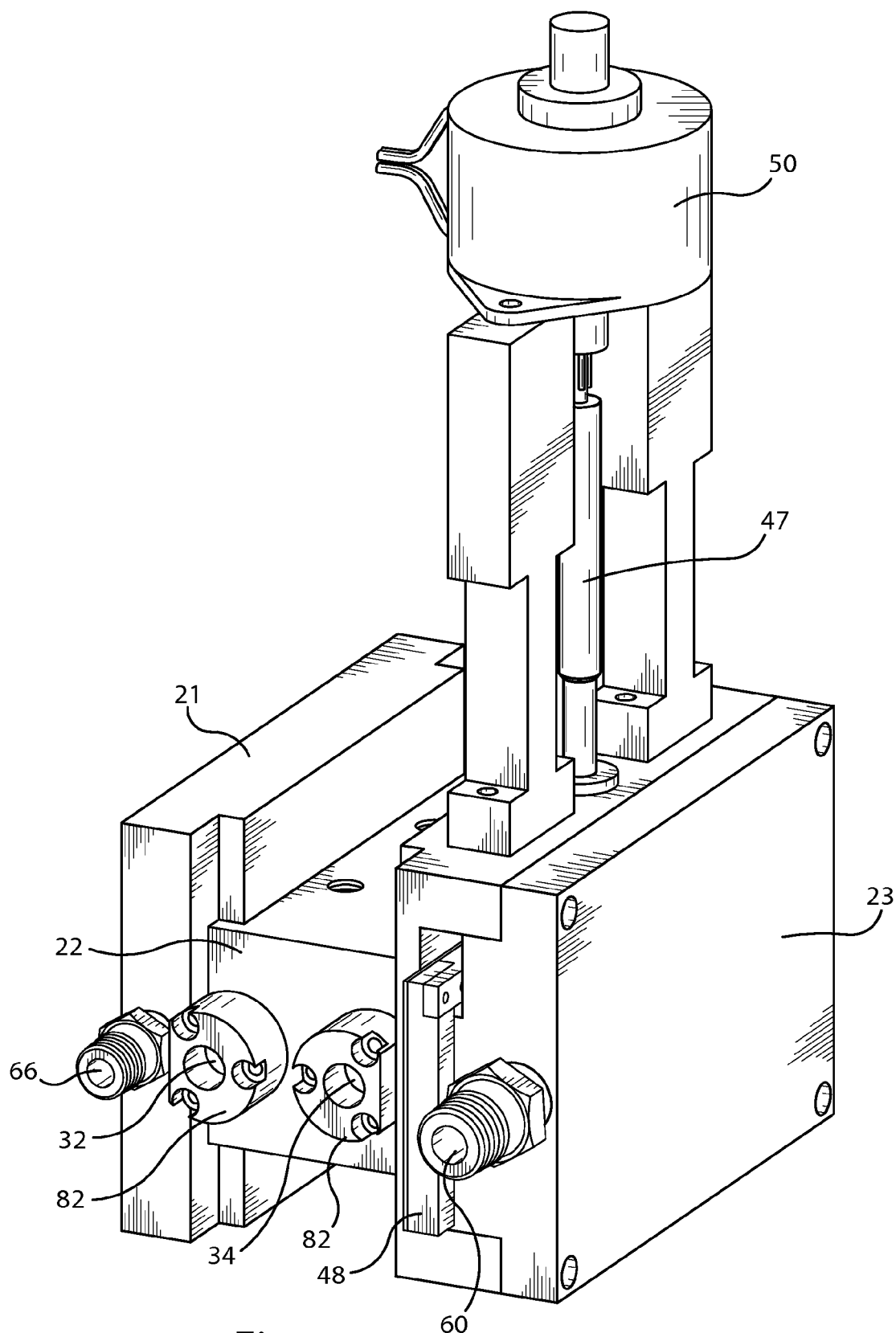
FIG. 7 is a perspective schematic view of the sensor assembly.

The sensor assembly is shown schematically in FIGS. 1, 3 and 7. The core of the sensor assembly 20 is a cavity spacer 22 machined from a single block of Invar (low thermal expansion steel). The cavity spacer 22 is flanked on one side by a first housing 21 and on an opposite side by a second housing 23. The spacer 22 has a narrow slot 24 that houses a diffusion column 26 with multiple mounting points 28 and 30 for the high reflectivity mirrors that form the optical cavities 32 and 34 in combination with holes that allow an optical cavity mode (schematically shown as 33 and 35 in FIG. 3) to pass through the cavity spacer 22. The diffusion column 26 is formed by attaching two plates 36 and 38 into the slot 24 in the cavity spacer 22. The plates 36 and 38 are secured using screws to the spacer 22 with O-rings around the screws to seal the assembly from the environment. The inside surface of the plates 36 and 38 are coated with any of a variety of stationary phases used for Wall-Coated Open Tubular (WCOT) or Porous-Lay Open-Tubular (PLOT) GC columns including, but not limited to molecular sieve, polyamide, polystyrene-divinylbenzene, carbon, polysiloxane, or polyethylene glycol (PEG) layers and coatings. The plates 36, 38 may be removed and replaced with different plates independently of the changing of other components of the sensor assembly 20 to provide a diffusion column 26 with different properties.

Figure 9A:
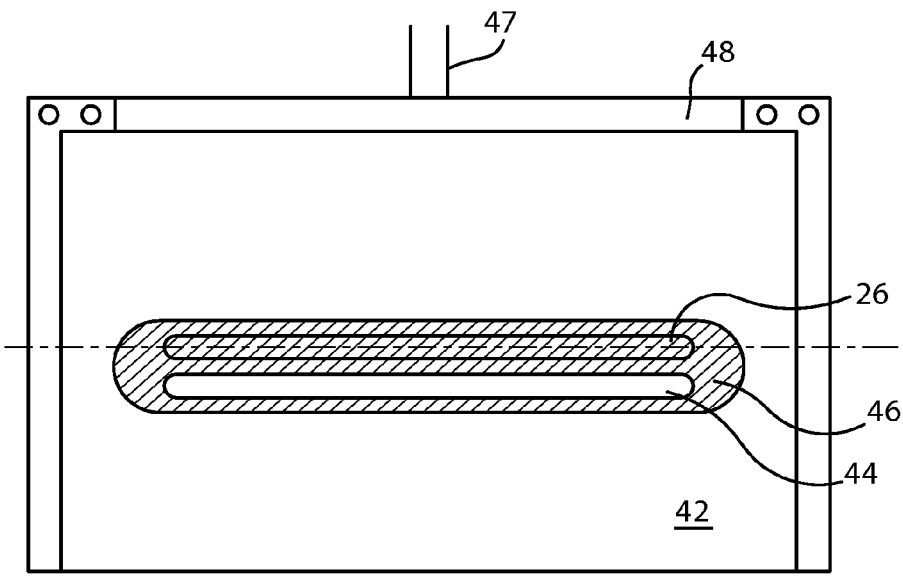
FIGS. 9a and 9b are schematic representations of the operation of a sliding gate.
Figure 9B:
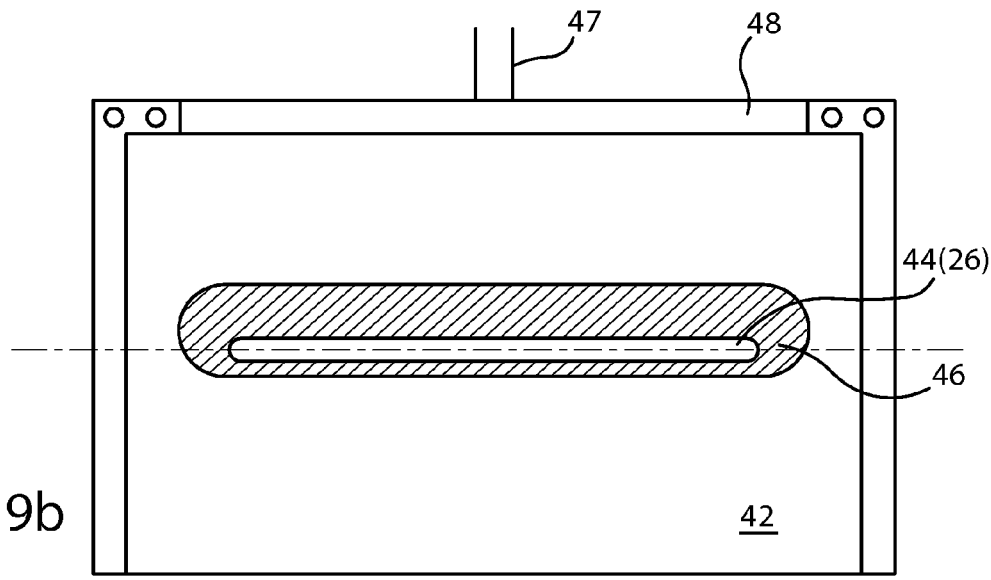

Mounted to the Invar spacer 22 is the loading chamber hardware 40 and a gate 42. An O-ring 69 seals the cavity spacer 22 to the second housing 23, which contains the loading chamber. The gate 42 is a thin steel sheet with a machined slot 44 and is attached to a rod 47 via a rectangular coupler 48. A linear drive stepper motor 50 drives the rod 47 to open and close the gate 42 (as indicated by arrows in FIG. 1). Referring additionally to FIGS. 9a and 9b, by actuating the gate 42, the slot 44 can be aligned with the diffusion column 26 (open) or sealed against the PTFE pads 46 (closed) to isolate a sample loading chamber 60 from the diffusion column 26. The gate 42 is sealed on both sides with O-rings 52, 53 so that the column can be operated under pressure/vacuum relative to ambient conditions and to prevent contamination from ambient gas. When the gate 42 is opened, diffusion from the loading chamber 60 into a first end 62 of the diffusion column 26 occurs. The other end 64 of the diffusion column 26 is attached to a chamber 66 that allows the buffer to be purged and replaced. An O-ring 68 seals the cavity spacer 22 to the first housing 21, which contains the chamber 66. Cavities 32 and 34 interact with a volume of the diffusion column which runs parallel to the plane of the gate and the center of each cavity is a constant distance from the gate.

The details of the mirror mounting system 70 can be seen in FIG. 3. A high finesse mirror 72 is glued into a ring 74 of kovar (a steel alloy with CTE matched to the fused silica mirrors) to form a mirror assembly 76. These mirror assemblies 76 are mounted to the cavity spacer 22. Each cavity (pair of high finesse mirrors) has one PZT (Piezoelectric) actuator 78. Lasers 80 are provided at the same or opposite end of the cavity from the PZT actuator 78 and provide light initially in the direction shown by arrows "A" and "B". The PZT actuator 78 is used to change the length of the optical cavity 32 or 34 as needed to ensure that the resonant optical frequency of each cavity 32 and 34 is coincident with the laser 80 optical frequency (i.e. speed of light divided by the wavelength). The PZT actuator 78 is secured to the cavity spacer 22 using a thin layer of high strength epoxy. The side of the kovar ring 74 that contacts the cavity spacer 22 or PZT actuator 78 is coated with a removable silicone adhesive. This adhesive serves to seal the mirror assembly 76 to the spacer or PZT, however, mechanical strength will be provided by compressing the mirror assembly 76 to the spacer using a mirror cap 82. The mechanical compression also improves PZT actuator 78 performance. This design allows the mirrors 72 to be replaced easily, which is advantageous for field deployment of this device. The mirrors 72 can be provided with a cover attached to the silicone adhesive that can be removed immediately prior to installation of the mirror to prevent contamination of the mirror surface with dust or other foreign matter. The mirrors may be easily replaced in the instance that they become damaged or contaminated.

The cavity mirrors 72 will generally be super-polished plano-concave mirrors with the curved surface coated with a high-reflectivity dielectric stack with transmission and absorption loss of a few parts per million with exact numbers depending on the operating wavelength and anticipated total absorption in the cavity. The plano side of the mirror is typically Broad Band Anti-Reflection (BBAR) coated and may be tilted relative to the concave surface of the mirror at the design point of incidence of the optical beam to prevent optical interference among multiple reflections (known as etalon effects) within the mirror.

Figure 10:
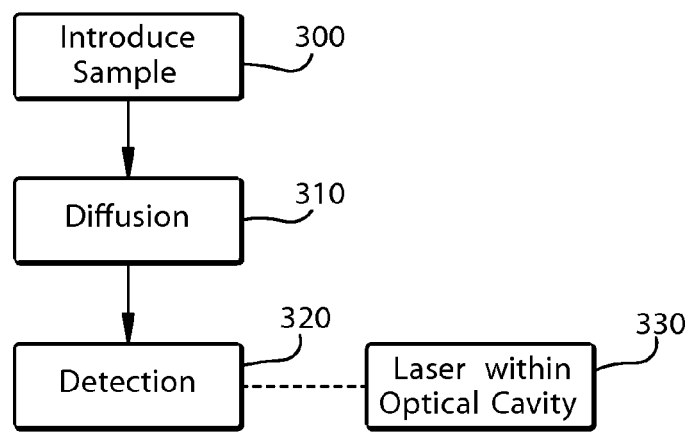
FIG. 10 is a flowchart showing a method of operation.

In general, referring to FIG. 10, a first step 300 includes introducing a sample into the sensor assembly, followed by a step 310 of allowing the sample to diffuse in a diffusion column. This is followed by a step 320 of detecting an analyte of interest in the diffusion column. Typically this is done in a step 330 utilizing a laser exciting an optical cavity and associated detector.

Referring back to FIGS. 1 and 3, at the beginning of a cycle, the sample loading chamber 60 is filled with a sample gas as shown by arrow "C" in FIG. 3. The sample gas will typically consist of a large component of a gas that is not of general interest, e.g. standard ambient atmosphere, and traces of the molecules of interest (analytes). The diffusion column 26 is filled with a buffer via the buffer loading chamber 66 which may be the same or different from the dominant component of the sample gas. The buffer may be either devoid of analytes or have a known concentration of analytes. The buffer gas may be changed (as shown by arrow "D" in FIG. 3) between different testing events based on the masses of the analyte species to be detected. The gas-tight gate 42 separates the diffusion column 26 and loading chamber 60. At a specified time, an electromechanical actuator, typically the stepper motor 50, opens the gate 42 bringing the buffer and sample into contact, at which point the sample/buffer gas mixture will begin to diffuse into the buffer contained within the diffusion column 26. The position of the gate 42 is recorded (here indirectly and optically with an LED 84 and photodiode 86) to determine the exact time of the gate opening. The time is stored on typical memory components (not illustrated)

While the sample is diffusing down the diffusion column 26, the detection signals (e.g. the optical absorption signals) of the analytes are recorded (and stored in the memory components previously described) at one or more distances (X, Y, etc) down the diffusion column (the measurements will typically be integrated concentrations along lines parallel to the gate 42). As molecules diffuse down the diffusion column 26, they encounter and partition into stationary phase 39 (indicated with random hatching in FIG. 3), which lines the walls of diffusion column 26. The molecules spend a fraction of time adsorbed in the stationary phase, with the fraction depending on the geometry of the diffusion column 26 and partition coefficient of the molecule in the stationary phase given the particular stationary phase coating on the walls.

During the course of the diffusion measurement, the temperature of the sensor assembly 20 may be held constant or varied according to a specific temperature program. The temperature may be controlled (via heating/cooling) using one or more thermo-electric coolers 88 (TECs) in a servo configuration, while the temperature is monitored using one or more temperature sensing elements 90, e.g. thermistors, mounted in thermal contact with the sensor assembly 20. During the measurement the pressure of the sample will be monitored constantly by pressure transducers 104 and 112. Using known controls the temperature and pressure may be actively stabilized. Both pressure and temperature information are required to convert total absorption to concentration, however relative concentrations of analytes can be extracted without complete pressure and temperature information. In applications where absolute concentrations are not required, this will simplify the detection. To enact a cleaning of the device, the sensor may be operated at an elevated temperature for a select period of time.

Figure 2:
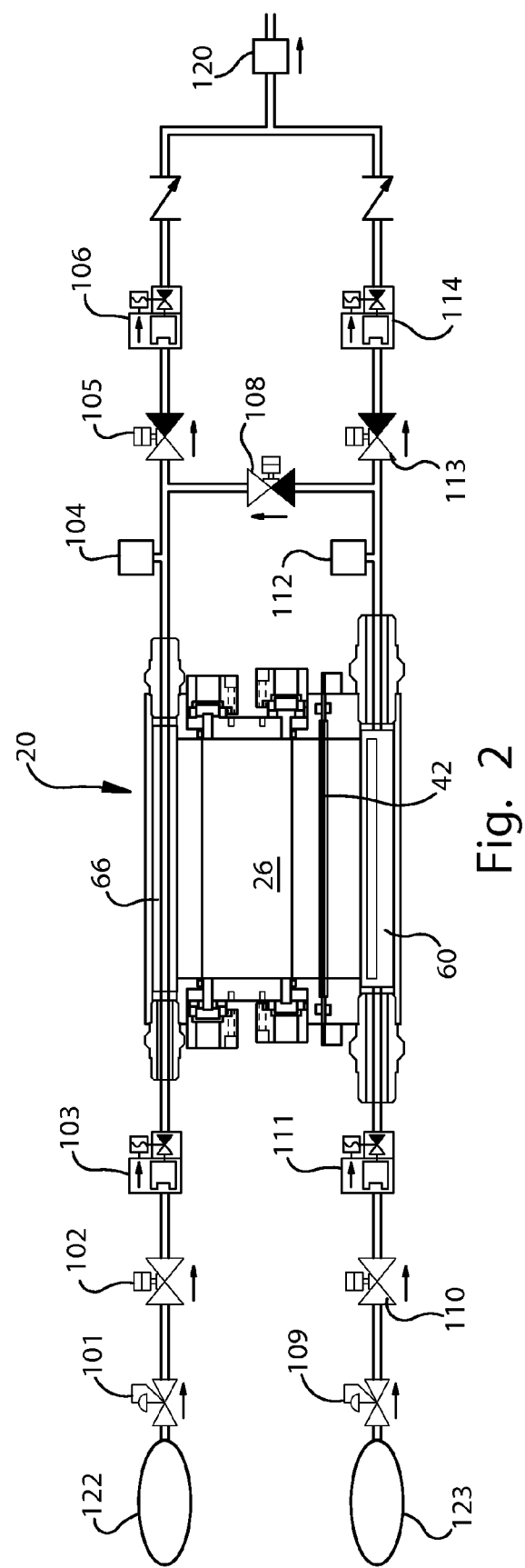
FIG. 2 is a schematic representation of the movement of sample gas and buffer gas within the sensor assembly.

One specific cycle, designed to perform repeated, closely spaced measurements on an ambient atmosphere uses the hardware shown in FIG. 2 to prepare sample and buffer gases. The gas cycle operates as follows. During the diffusion measurement, all valves are closed except for equilibration solenoid valve 108 which is open. At the conclusion of a diffusion measurement, the gate 42 is closed. Solenoid valves 105 and 113 are opened, proportional valves 106 and 114 are opened to their maximum, and solenoid valve 108 is closed. Vacuum pump 120 evacuates both the diffusion column 26 and the sample loading chamber 60. When a set pressure is reached, the proportional valves 106, 114 partially close to reduce flow to a set level, and solenoid valves 102, 110 and proportional valves 103, 111 open to set levels allowing flow from a pressurized bottle 122 (or alternative source described later) containing the buffer with pressure reduced by regulator 101 and the sampled atmosphere 123 potentially with pressure reduced by regulator 109 into the sensor assembly. This will introduce the required gases and also act as a purge of the system. During this stage of the cycle, the pressures in the chambers 60, 66 are allowed to reach a level higher than pressure during the diffusion measurement. Once the purge is complete, the valves 101, 102, 110, 111 close and the proportional valves 106, 114 close to a set level so that the pressure decreases slowly in the system. When the target pressure for the system is reached in the loading chamber 60 (diffusion column) as monitored by the pressure gauges 104, 112 mounted to the buffer gas line and sample gas line immediately downstream of the sensor assembly 20 and directly communicating with the gas in the buffer 66 and sample 60 loading chambers, the respective solenoid and proportional valves 113, 114 or 105, 106 will close. When both chambers 60, 66 have reached the approximate target operating pressure, the equilibration solenoid valve 108 opens, forming a direct connection between the loading and diffusion channels to equilibrate the pressure between the two, but far enough from the diffusion region so as not to contaminate the measurement. The system is now prepared for the measurement portion of the cycle of operation.

The sample loading chamber 60 may be filled actively as described above from a previously captured sample. Alternatively, using a known sampling device, a sample may be drawn from the surrounding atmosphere and directed to the sample loading chamber 60. In a similar manner buffer gas may be drawn from the surrounding atmosphere and brought into a desirable condition via treatments by filters, adsorption or catalytic conversion, before transfer to the buffer loading chamber 66.

Referring back to FIGS. 1 and 3, measurements in the diffusion column 26 to determine species present in the sample are performed using optical absorption. Specifically, the total optical absorption is measured at fixed locations (X, Y, etc.) in the diffusion column by having the diffusion column traverse the optical mode of one or more high finesse (F=105) Fabry-Perot optical cavities 32, 34, however any sufficiently sensitive measurement is consistent with this invention. The presence of high finesse cavities 32 and 34 increases the effective path length of the measurement significantly allowing for the measurement of exquisitely low absorptions, with the Noise Immune Cavity Enhanced-Optical Heterodyne Molecular Spectroscopy (NICE-OHMS) technique showing detection sensitivity of $5\times10^{-13}$ cm$^{-1}$/Hz$^{1/2}$ (J. Ye, L.-S. Ma, and J. L. Hall, (1998)), Other techniques including Direct Cavity Transmission (DCT) or integrated cavity output spectroscopy (ICOS) (O'Keefe et al (1999)) can be employed, but Cavity Ring-Down Spectroscopy (CRDS) is described here (Berden, G., and J. Engeln (2009)). An optical frequency comb can also be coupled to the cavity to perform simultaneous measurements at many optical frequencies (Thorpe, M. et al (2008), CRDS accesses optical absorption by measuring the decay time, T, of light within the cavity. The decay time is a function of intrinsic (not sample related) losses in the system and optical absorption and scattering of the species in the cavity. In this embodiment, it is unnecessary to carefully calibrate the "bare cavity" ring-down time because the Bayesian estimation scheme allows for the estimation of the bare cavity decay during each diffusion cycle by adding to the estimator a single parameter for each laser wavelength representing non-time dependent bare cavity absorption (Stockton, J. K., and Tuchman, A. K. (2009)).

Figure 4:
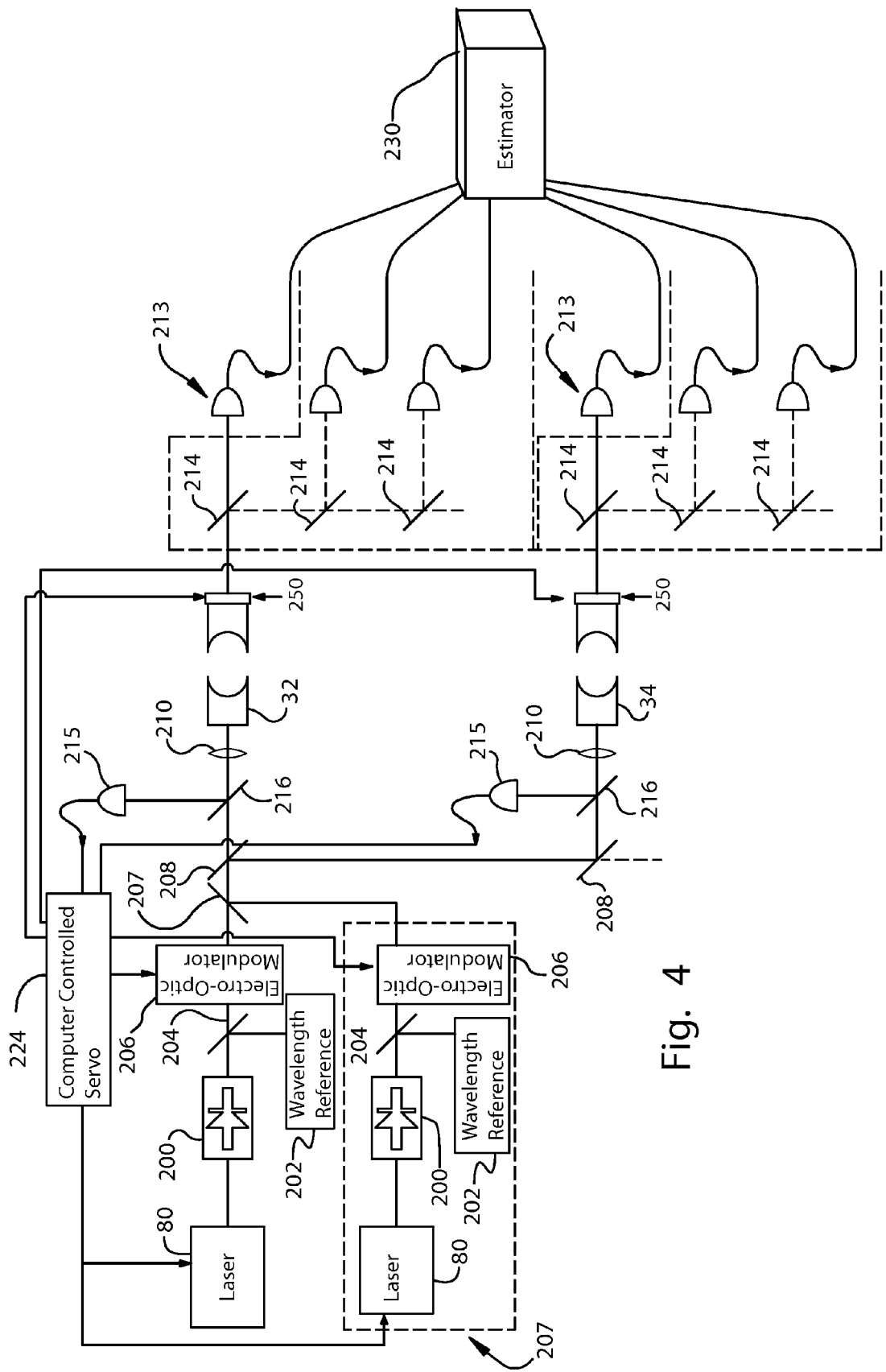
FIG. 4 is a schematic view of optics and laser electronics used with the sensor.

Referring to FIG. 4, the laser scheme to perform CRDS is as follows: Light from the laser diode source 80 (e.g. a temperature stabilized DFB type laser) passes through an optical isolator 200. The wavelength of the laser may be chosen based on the properties of the species to be detected or may be selected based on a history of previous measurements. A fraction of the light is sent to a wavelength reference 202 (e.g. vapor cell or other frequency reference). The reference is fed to the laser electronics that set the laser frequency to the desired frequency by varying the laser temperature and current. The fraction that does not pass into the wavelength reference (the majority of the light) passes into a single mode, polarization maintaining optical fiber 204. The fiber is coupled to a waveguide Electro-Optic (phase) Modulator (EOM) 206 chosen for wide bandwidth electro-optical response.

Figure 5:
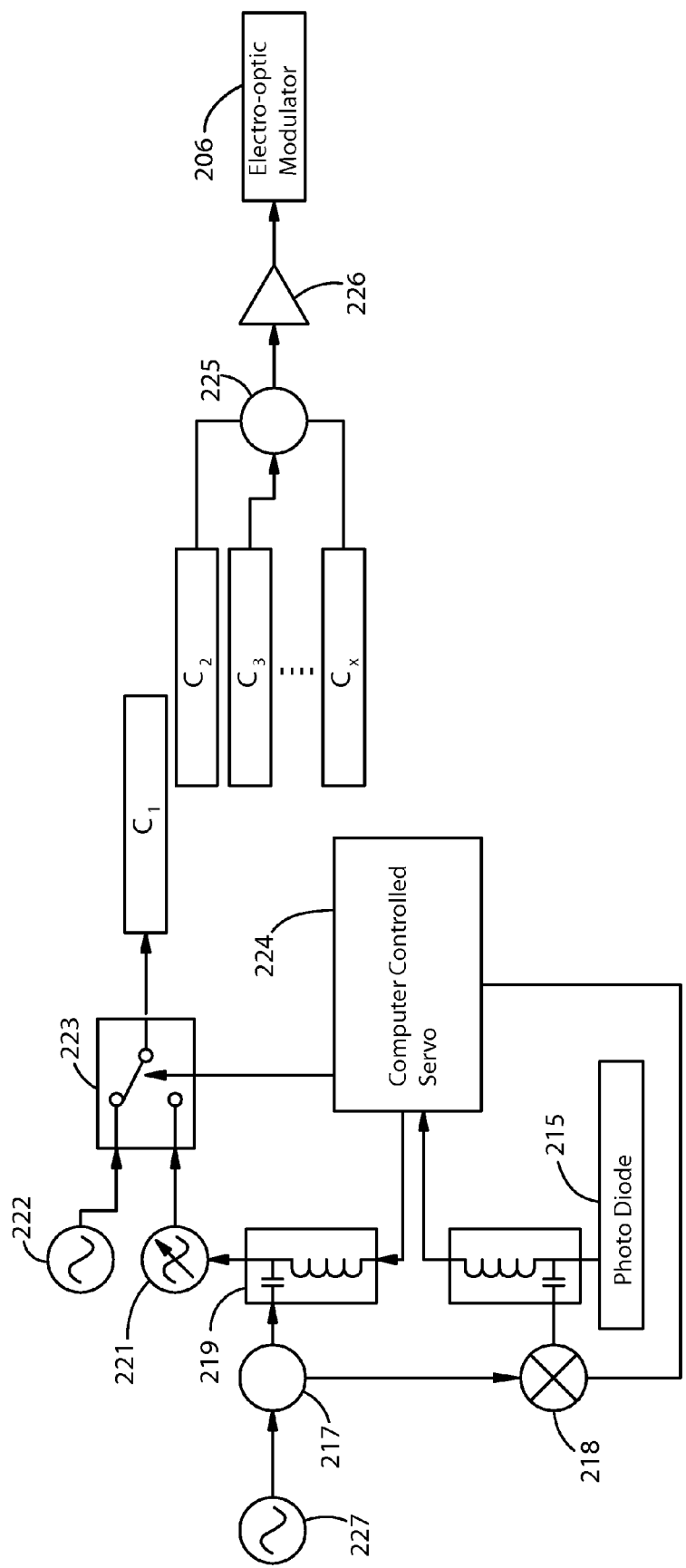
FIG. 5 is a schematic of radio frequency components for laser locking used with the sensor.

Referring to FIG. 5, the EOM 206 is driven with frequency modulated radio-frequency (RF) signals that allow locking of optical sidebands to an optical cavity (Mabuchi, H., Ye, J., & Kimble, H. J. (1999)). By locking optical sidebands to the cavity instead of the optical carrier frequency (the unmodulated optical frequency emitted directly from the laser), the EOM 206 can effect very fast feedback to the sideband frequency, facilitating laser locking. Locking the laser carrier frequency itself is often not feasible for the case of e.g. DFB lasers, because the laser frequency cannot be made to respond quickly enough to maintain frequency locking to the cavity. Use of the sideband enables the use of broad linewidth lasers with slow feedback that would otherwise be impossible to lock to the cavity. In addition, the EOM sideband lock greatly simplifies laser switching for ring-down initiation. A ring-down is initiated by turning off the RF drive for the particular sideband coupled to the cavity. Because of the wide bandwidth of the EOM 206, the switching can be extremely rapid, thereby avoiding complications in ring-down measurement due to slow switching of the light, and also facilitates reacquisition of the lock. Different cavities may be locked to different sidebands generated by driving the EOM 206 with multiple frequency modulated RF signals, or all cavities may be locked to the same sideband. When more than one cavity is employed, it is possible to alternate which cavity is ringing down so that each laser is constantly locked to at least one cavity. For these lock schemes, the EOM 206 is used for high frequency stabilization of the laser, i.e. "linewidth narrowing," and the PZT 250 (see FIG. 4) attached to the cavity is used to tune the length of the cavity to resonate the target optical frequency.

Referring back to FIG. 4, after the light exits the EOM 206, it is combined with light from any additional laser systems 201, each of which can have a separate isolator and EOM with associated RF electronics. The combining of lasers can, for example, be accomplished in free space using dichroic optics 207 to minimize power loss. This light is then divided among the several cavities 32, 34 using beamsplitters 208 of varying reflection/transmission ratios depending on the number of cavities and the desired distribution of optical power among them. The light passes through mode-matching optics (lenses) 210 to couple maximally to the TEM00 mode of each optical cavity 32, 34. Light reflected from the cavity 32, 34 bounces off a beam pickoff 216 and is detected using an amplified photodiode 215.

The laser frequency is locked to the resonance frequency of the optical cavity 32, 34 using the RF circuit shown in FIG. 5. An oscillator 227 generates a radio frequency f1. This frequency is split into two components using a zero-degree splitter 217. This radio frequency signal is combined with the computer controlled servo 224 output with bias-T 219. The combined signal drives the control port of a Voltage Controlled Oscillator (VCO) 221. The output frequency f2 of VCO 221 is fed into a Single Pole Double Throw (SPDT) radio frequency switch 223. Also fed into the RF switch is the output of a dummy oscillator 222 whose output frequency f3 is different from f1 and f2 and whose output level is the same as the output of VCO 221. Dummy oscillator 222 maintains constant RF power to the EOM 206 but does not couple light into any cavity; this eliminates thermal effects in the EOM caused by switching power levels incident on this device. The output of the RF switch 223, associated with a first circuit C1 is combined with the outputs of other similar circuits C2, C3 . . . CX in a combiner 225, amplified in an amplifier 226 and sent to the EOM 206. One such circuit is used for each cavity/laser pair. The laser is stabilized to the cavity by mixing the output of the lock photodiode 215 with the one of the outputs of the splitter 217 on a radio frequency mixer 218. The output of the mixer is the error signal that is fed into the computer controlled servo 224 to produce the servo output that feeds into VCO 221 as described above. The servo output controls the center frequency of the VCO (f2) which then controls the frequency of the laser sidebands created by the EOM, keeping one of the laser sidebands resonant with the cavity. A ring-down event is initiated by switching the RF switch to the dummy rf, which switches the laser sideband out of resonance with the optical cavity. At very low frequencies, the computer controlled servo 224 also tunes the length of the cavity using the PZT 78.

Referring back to FIG. 4, the light transmitted through a cavity 32, 34 is detected on a series of amplified photodiodes 213, with one photodiode for each laser wavelength. The different laser wavelengths are separated using dichroic optics 214 or dispersive optical element(s) such as a grating or prism. The detectors are used to record the cavity ring-down signal for each wavelength. The output signal is digitized and analyzed in software (illustrated as part of the estimator 230 described below) to find the ring-down time τ using, for example, a nonlinear least squares algorithm.

Many ring-down measurements are performed during each diffusion shot (sample run). The ring-downs are performed as quickly as possible as constrained by the ring-down time τ of the optical cavity. For best signal to noise, each ring-down trace must be recorded for several τ before the sideband is turned back on. In an embodiment with a cavity of Finesse ~$10^5$ and cavity length of 10 cm, a ring-down event is triggered every 200 microseconds while the duration of a single diffusion shot is several seconds.

The calculated τ values are input into a Bayesian estimator 230 that uses the recorded τ values over an entire trial to determine the concentrations of species with different effective diffusion coefficients. The use of either multiple columns and or multiple laser wavelengths will increase the ability of this sensor to differentiate species that have the same diffusion coefficient in any one column by increasing the amount of information available to the Bayesian estimator 230. The Bayesian estimator 230 uses differences in diffusion and optical absorption between the columns/laser wavelengths to estimate the concentrations of species that would otherwise be indistinguishable. The sensor device may include an optical or audible alarm that is triggered when the presence or specific level of a certain species is detected. The Bayesian estimator 230 may include a program storage medium readable by a computer.

Example

Figure 6:
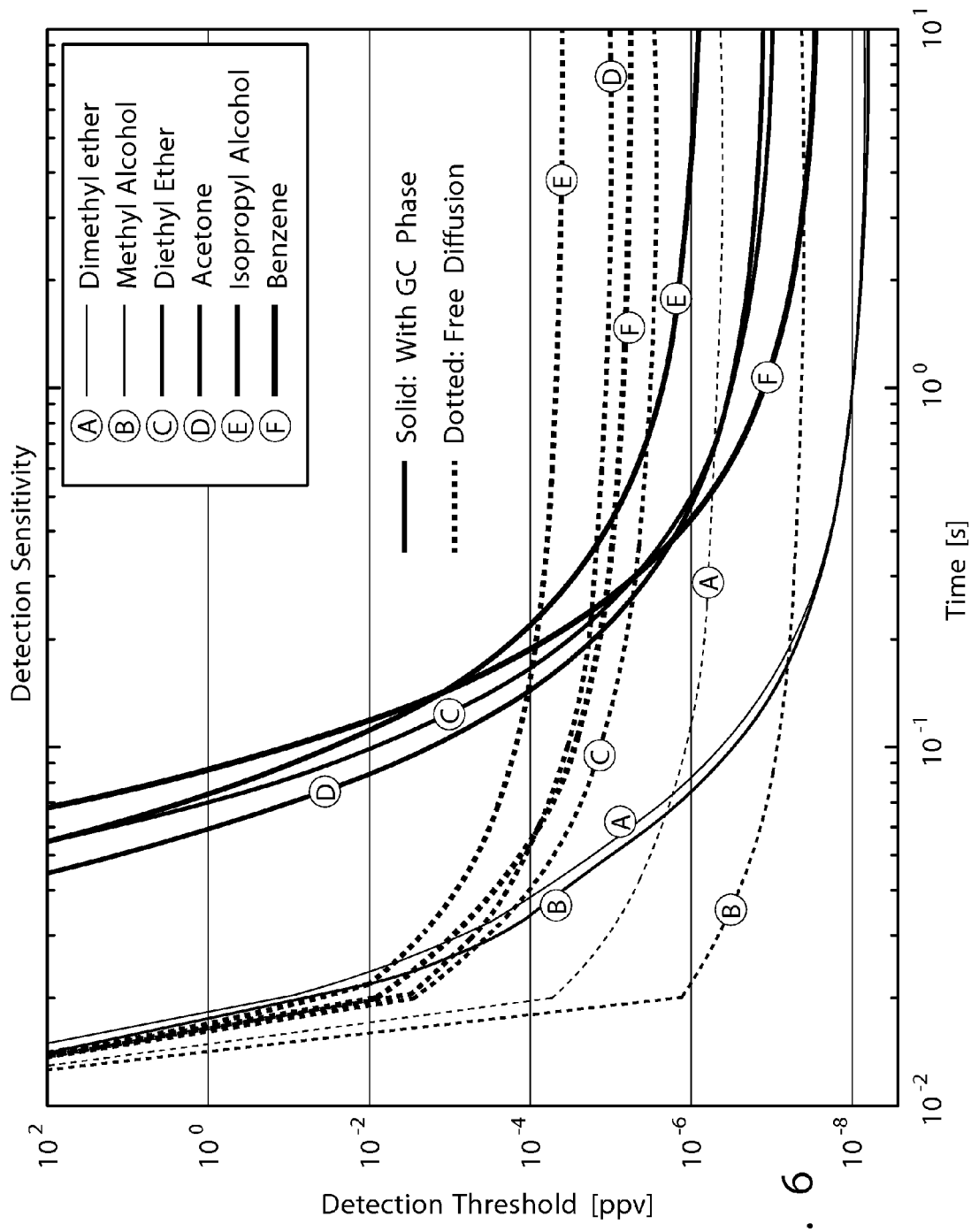
FIG. 6 is a graph showing detection thresholds of analytes both using the sensor assembly and not using the sensor assembly.

The efficacy of the use of GC stationary phases has been evaluated through numerical simulations using cavity detection sensitivity numbers measured in the apparatus without the use of a stationary phase. This detection sensitivity is $10^{12}$ cm$^{-1}$/Hz$^{1/2}$. The simulation (FIG. 6) shows the detector sensitivity, in parts per unity by volume (ppv) as a function of the diffusion time. In one second the detector has approached final sensitivity and by 10 seconds optimal sensitivity has been reached. The use of the GC phase leads to nearly two orders of magnitude improvement in sensitivity at the expense of slightly longer measurement times. The final benefit of the GC phase is summarized in Table 1 below, which shows the sensitivity after 10 seconds of diffusion.

TABLE 1

| Compound | Sensitivity with GC (ppb) | Sensitivity without GC (ppb) |
| --- | --- | --- |
| Dimethyl ether | 5.5 | 380 |
| Methyl Alcohol | 6 | 38 |
| Diethyl Ether | 76 | 2500 |
| Acetone | 100 | 9000 |
| Isopropyl Alcohol | 675 | 38000 |
| Benzene | 20 | 5000 |

In maintenance practice, the sensor device 20 is calibrated by using a known gas and placing it within the sample loading chamber 60. If the known analyte is not detected at all or not in the proper amount, the device 20 may be cleaned by high temperature operation or by replacement of one or more of the plates 36, 38 with the stationary phase thereon.

Figure 8A:
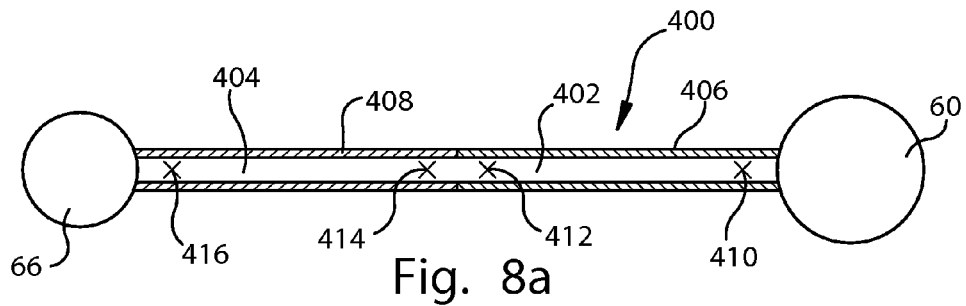
FIG. 8a is a schematic of an alternative diffusion column.

As an alternative shown in FIG. 8a, a single diffusion column 400 may comprise multiple sections 402 and 404, aligned linearly, wherein each section includes a different stationary chromatography phase 406 and 408. Several measuring points (optical cavities) 410 and 412 may be placed in the first section 402 and several measuring points 414 and 416 may be placed in the second section 404.

Figure 8B:
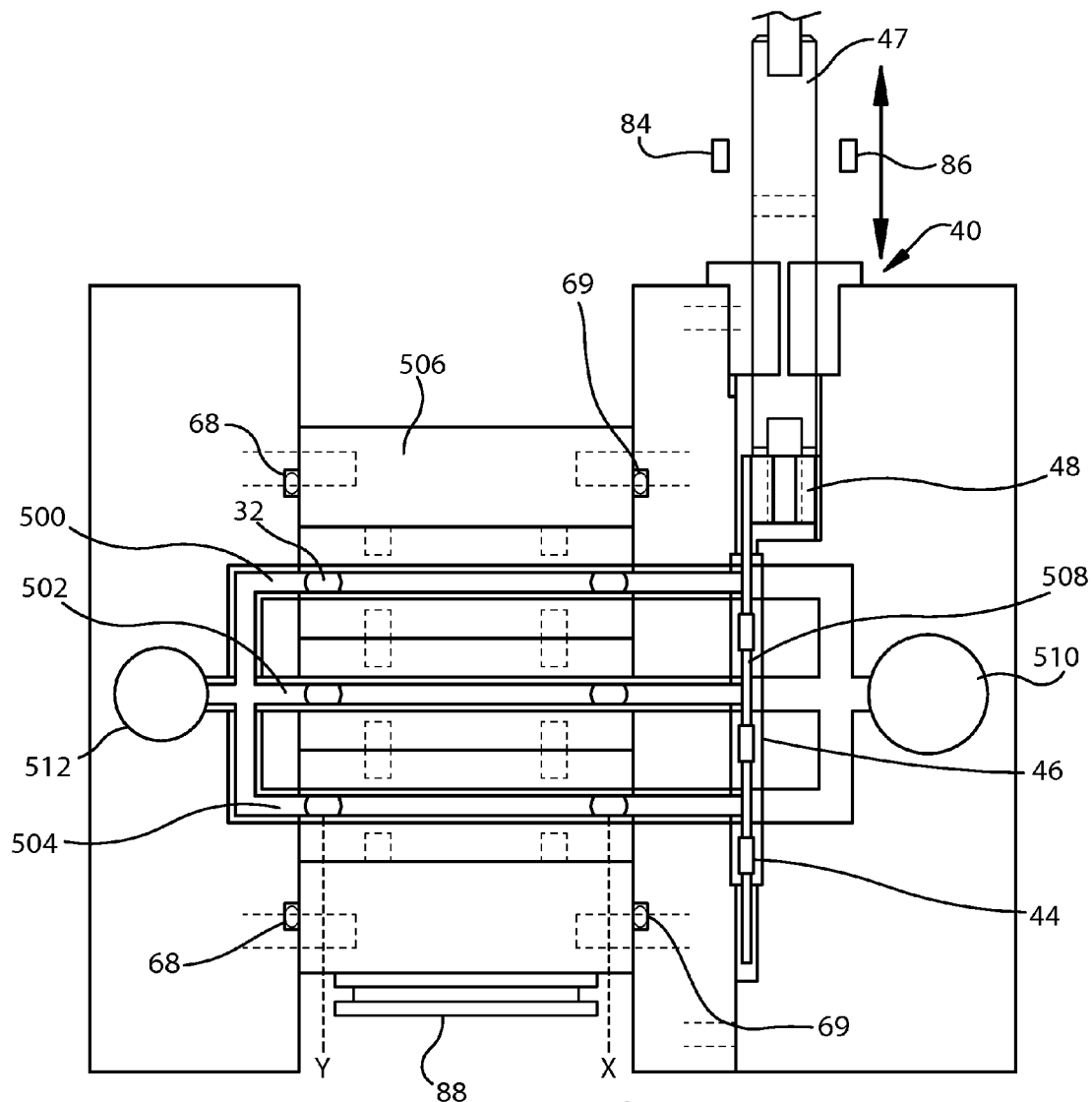
FIG. 8b is a schematic of an alternative sensor assembly with multiple diffusion columns.

As an alternative shown in FIG. 8b, several diffusion columns 500 and 502 and 504 may be arranged side by side in a cavity spacer 506. A gate 508 is provided with three openings so sample material from a sample chamber 510 may reach each of the diffusion columns at a known time. Additionally, passages are provided so buffer from a buffer chamber 512 may also reach each diffusion column. Each diffusion column is provided with its own dedicated optical cavities (not illustrated).

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

REFERENCES

J. Ye, L.-S. Ma, and J. L. Hall, "Ultrasensitive detections in atomic and molecular physics: demonstration in molecular overtone spectroscopy," J. Opt. Soc. Am. B, vol. 15, no. 1, pp. 6-15, 1998.

Berden, G., and J. Engeln, Cavity Ring-Down Spectroscopy: Techniques and Applications. Oxford: Blackwell, 2009

Stockton, J. K., and Tuchman, A. K. "Bayesian estimation for selective trace gas detection." Appl. Phys. B. 96 (2009): 567-570. Also WO 2010/042178 A2

Mabuchi, H., Ye, J., & Kimble, H. J. (1999). Full observation of single-atom dynamics in cavity QED. Applied Physics B Lasers and Optics, 1108, 1095-1108.

Anthony O'Keefe, James J. Scherer, and Joshua B. Paul, "cw Integrated cavity output spectroscopy," Chem. Phys. Lett., vol. 307, p. 343-349 (1999).

Thorpe, M., Balslev-Clausen, D., Kirchner, M. S., and Ye, J., "Cavity enhanced optical frequency comb spectroscopy." Optics Express, 16 p. 2387 (2008).

We claim:

1. A chromatography sensor device comprising:
a loading chamber configured to receive a sample fluid;
a diffusion column configured to communicate with the loading chamber, wherein the diffusion column has walls lined with a chromatography stationary phase material, and wherein the chromatography stationary phase material lining the walls defines a pathway through the diffusion column that is configured to contain a buffer fluid;
a gate that divides the diffusion column from the loading chamber, wherein the gate is configured to be opened to allow the sample fluid in the loading chamber to diffuse through the diffusion column without being transported by a mobile phase; and
one or more analyte detection devices located at fixed distances from the gate, said analyte detection devices being configured to detect an analyte in sample fluid as it diffuses through the diffusion column.

2. The device of claim 1, wherein the buffer fluid is a gas and the sample fluid is a gas.

3. The device of claim 1, wherein the buffer fluid is a liquid and the sample fluid is a liquid.

4. The device of claim 1, further comprising an estimator that receives signals from the detection devices and provides estimated concentrations of different analyte species present in the sample fluid.

5. The device of claim 1, wherein the diffusion column is formed from two removable plates supported in a monolithic spacer.

6. The device of claim 1, further including one or more additional diffusion columns configured to communicate with the loading chamber, wherein each diffusion column of the device has walls that are lined with a different chromatography stationary phase material.

7. A method for estimating the concentration of different molecules present in a sample fluid, the method comprising the steps of:
providing a chromatography sensor device according to claim 1;
introducing a sample fluid into the loading chamber of the chromatography sensor device;
opening the gate that divides the diffusion column from the loading chamber;
allowing the sample fluid to diffuse along the diffusion column lined with the chromatography stationary phase and containing the buffer fluid without entraining the sample fluid in a mobile phase; and
detecting analytes present in the sample fluid using detectors provided at two or more fixed distances from the gate.

8. The method of claim 7, wherein the buffer fluid is a gas and the sample fluid is a gas.

9. The method of claim 7, wherein the buffer fluid is a liquid and the sample fluid is a liquid.

10. The method of claim 7, wherein the loading chamber and the diffusion column are operated at pre-determined fixed temperatures.

11. The method of claim 7, wherein the loading chamber and diffusion column are operated at programmed time-varying temperatures.

12. The method of claim 7, wherein the step of detecting comprises:
exciting first and second optical cavities communicating with the diffusion column with light from one or more lasers; and
detecting optical absorption losses at laser wavelengths in the optical cavities using the detectors.

13. The method of claim 12 wherein the detection step further comprises:
estimating a concentration of different molecules present in the sample fluid based on detected absorption losses as a function of time.

14. A chromatography sensor device comprising:
a loading chamber configured to receive a sample fluid;
a diffusion column configured to communicate with the loading chamber, wherein the diffusion column has walls lined with a chromatography stationary phase material, and wherein the chromatography stationary phase material lining the walls defines a pathway through the diffusion column that is configured to contain a buffer fluid;
a gate that divides the diffusion column from the loading chamber, wherein the gate is configured to be opened to allow the sample fluid in the loading chamber to diffuse through the diffusion column without being transported by a mobile phase;
a first optical cavity communicating with the diffusion column at a first distance from the gate;
a second optical cavity communicating with the diffusion column at a second distance from the gate; and
detection devices associated with each optical cavity, said detection devices being configured to detect an analyte in sample fluid as it diffuses through the diffusion column.

15. The device of claim 14, further comprising a second loading chamber configured to receive a buffer fluid, and wherein the diffusion column is configured to communicate with the second loading chamber.

16. The device of claim 14, wherein the buffer fluid is a gas and the sample fluid is a gas.

17. The device of claim 14, wherein the buffer fluid is a liquid and the sample fluid is a liquid.

18. The device of claim 14, further comprising a plurality of mirrors associated with each optical cavity and a removable mirror cap associated with each optical cavity which is removable to allow for replacement of said plurality of mirrors.

19. The device of claim 18, further comprising a PZT actuator associated with each optical cavity that moves at least one mirror in order to adjust an optical cavity mode.

20. A chromatography sensor device comprising:
a loading chamber configured to receive a sample fluid;
a diffusion column configured to communicate with the loading chamber, wherein the diffusion column has walls lined with a chromatography stationary phase material, and wherein the chromatography stationary phase material lining the walls defines a pathway through the diffusion column that is configured to contain a buffer fluid;
a gate that divides the diffusion column from the loading chamber, wherein the gate is configured to be opened to allow the sample fluid in the loading chamber to diffuse through the diffusion column without being transported by a mobile phase;
a first optical cavity communicating with the diffusion column at a first distance from the gate;
a second optical cavity communicating with the diffusion column at a second distance from the gate;
one or more lasers for generating laser frequencies for exciting the first and second optical cavities; and
detection devices associated with each optical cavity, said detection devices being configured to detect an analyte in sample fluid as it diffuses through the diffusion column.

21. The device of claim 20, wherein the buffer fluid is a gas and the sample is a gas.

22. The device of claim 20, wherein the buffer fluid is a liquid and the sample fluid is a liquid.

23. The device of claim 20, wherein only one laser is used within the device, and the device further includes an optical frequency comb in optical communication with each cavity.

24. The device of claim 20, further comprising optics and electronics for locking frequencies of the lasers to resonant optical frequencies of the optical cavities.

25. The device of claim 20, wherein the diffusion column is formed from two removable plates supported in a monolithic spacer.

26. The device of claim 20, wherein the detection devices are configured to detect the absorption losses of the lasers in the optical cavities using either direct cavity transmission (DCT), cavity ring-down spectroscopy (CRDS), noise immune cavity enhanced-optical heterodyne molecular spectroscopy (NICE-OHMS), or integrated cavity output spectroscopy (ICOS).

* * * * *